(12) United States Patent
Bennion et al.

(10) Patent No.: US 10,845,369 B2
(45) Date of Patent: Nov. 24, 2020

(54) SAMPLING DEVICES AND METHODS OF USE

(71) Applicant: 3M INNOVATIVE PROPERTIES COMPANY, St. Paul, MN (US)

(72) Inventors: Nerys Bennion, Whitchurch (GB); James Watkin, Broadlands (GB); Russell M. I. Thomas, Treorchy (GB); William J. Simpson, Chippenham (GB)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 830 days.

(21) Appl. No.: 15/057,200

(22) Filed: Mar. 1, 2016

(65) Prior Publication Data

US 2016/0178639 A1 Jun. 23, 2016

Related U.S. Application Data

(62) Division of application No. 12/992,129, filed as application No. PCT/US2009/043748 on May 13, 2009, now abandoned.

(30) Foreign Application Priority Data

May 13, 2008 (GB) .................................. 0808557.3

(51) Int. Cl.
　　*C12Q 1/24* (2006.01)
　　*C12M 1/30* (2006.01)
　　*G01N 33/68* (2006.01)
　　*B01L 3/00* (2006.01)
　　*G01N 1/02* (2006.01)
　　*C12Q 1/66* (2006.01)
　　*C12Q 1/42* (2006.01)
　　*C12Q 1/48* (2006.01)

(52) U.S. Cl.
　　CPC ........ *G01N 33/6803* (2013.01); *B01L 3/5023* (2013.01); *C12Q 1/42* (2013.01); *C12Q 1/485* (2013.01); *C12Q 1/66* (2013.01); *G01N 1/02* (2013.01); *B01L 2200/16* (2013.01); *B01L 2300/069* (2013.01); *B01L 2300/0609* (2013.01); *G01N 2001/028* (2013.01)

(58) Field of Classification Search
　　None
　　See application file for complete search history.

(56) References Cited

U.S. PATENT DOCUMENTS

| | | |
|---|---|---|
| 3,169,905 A | 2/1965 | Lambert |
| 3,792,699 A | 2/1974 | Tobin et al. |
| 4,013,416 A | 3/1977 | Rittersdorf et al. |
| 4,728,499 A | 3/1988 | Fehder |
| 4,795,421 A | 1/1989 | Blasius, Jr. et al. |
| 4,978,504 A | 12/1990 | Nason |
| 5,266,266 A | 11/1993 | Nason |
| 5,827,675 A | 10/1998 | Skiffington et al. |
| 5,879,635 A | 3/1999 | Nason |
| 5,919,152 A | 7/1999 | Zygmont |
| 5,965,453 A | 10/1999 | Skiffington et al. |
| 6,180,395 B1 | 1/2001 | Skiffington et al. |
| 6,383,804 B1 | 5/2002 | Ward, Jr. et al. |
| 6,440,437 B1 | 8/2002 | Krzysik et al. |
| 6,524,530 B1 | 2/2003 | Igarashi et al. |
| 6,548,018 B2 | 4/2003 | DiCesare et al. |
| 6,867,342 B2 | 3/2005 | Johnston et al. |
| 7,399,984 B2 | 7/2008 | Feldsine et al. |
| 7,556,933 B2 | 7/2009 | Cairns et al. |
| 7,790,865 B1 | 9/2010 | Heath et al. |
| 2002/0057991 A1 | 5/2002 | Kelly et al. |
| 2003/0165550 A1 | 9/2003 | Rhoades |
| 2004/0267181 A1 | 12/2004 | Tuite et al. |
| 2005/0148044 A1* | 7/2005 | Rambach ................. C12N 1/20 435/34 |
| 2006/0216196 A1 | 9/2006 | Satoh et al. |
| 2009/0159442 A1 | 6/2009 | Collier et al. |
| 2010/0063004 A1 | 3/2010 | Chaudhuri et al. |
| 2010/0267124 A1 | 10/2010 | Inami et al. |

FOREIGN PATENT DOCUMENTS

| | | |
|---|---|---|
| EP | 0 105 747 | 4/1984 |
| EP | 1 298 069 | 4/2003 |
| EP | 1 333 097 | 8/2003 |
| GB | 1 371 417 | 10/1974 |
| GB | 2 358 061 | 7/2001 |
| JP | 8-327553 | 12/1996 |
| JP | 1-242519 | 9/1999 |
| JP | 2007-209223 | 8/2007 |
| JP | 2009-131474 | 6/2009 |
| JP | 2010/511723 | 4/2010 |
| WO | WO 1993/00994 | 1/1993 |
| WO | WO 1994/11528 | 5/1994 |
| WO | WO 1998/55094 | 12/1998 |
| WO | WO 2000/61105 | 10/2000 |
| WO | WO 2000/61106 | 10/2000 |

(Continued)

OTHER PUBLICATIONS

Hydratech—Specialist Fluid Solutions_Propylene Glycol, 2014.*

(Continued)

*Primary Examiner* — Sharmila G Landau
*Assistant Examiner* — Douglas F White
(74) *Attorney, Agent, or Firm* — Eric E. Silverman

(57) ABSTRACT

Sample-collecting devices, articles and methods of use are disclosed. Premoistened sample-collecting devices comprise 1,2-propanediol as a humectant, which promotes the retention of a liquid solution on the sample-collecting device during storage. 1,2-propanediol as humectant can be compatible with proteins and other reagents used to detect an analyte.

7 Claims, 3 Drawing Sheets

(56) References Cited

FOREIGN PATENT DOCUMENTS

| WO | WO 2000/61107 | 10/2000 |
|---|---|---|
| WO | WO 2001/054552 | 8/2001 |
| WO | WO 2006/069053 | 6/2006 |
| WO | WO 2007/069240 | 6/2007 |
| WO | WO 2009/134509 | 11/2009 |

OTHER PUBLICATIONS

Gürtler, V. et al.; "New approaches to typing and identification of bacteria using the 16S-23S rDNS spacer region"; Microbiology; vol. 142; 1996; pp. 3-16.

Rose, L. et al.; "Swab Materials and *Bacillus anthracis* Spore Recovery from Nonporous Surfaces"; Emerging Infectious Diseases; vol. 10, No. 6; 2004; pp. 1023-1029.

Brochure from Kensington Computer Products Group entitled "Surface Guardian® Cleaning Swabs"2008; 1 pg.

Brochure from Professional Disposal International entitled "Nice Pak, The Global Leader in pre-Moistened Wipes: Healthcare Information" 2008; 3 pgs.

Brochure from COPAN Diagnostics Inc. entitled "SRK Environmental Swab Systems" 8 pgs.

Cosby, N. et al.; "Custom Enzyme Substrates for Luciferase-based Assays"; Cell Notes; Issue 18, 2007; pp. 9-11.

Floeckher, J.; "Application Note—Swipe Assays", http://www.perkinelmer.corr/CMSResources/Images/44-73011APP_ABASwipeAssays.pdf. 2006 PDF file.

Mallmann, W.L. "A Critical Study of Various Types of Detergents and Disinfectants for Use in Dishwashing"; May 1937; Dishwashing, vol. 27; pp. 464-470.

Detergent Types; "University of TEESSIDE-School of Science and Technology-Science in your Home"; date unknown; 5 pgs.

\* cited by examiner

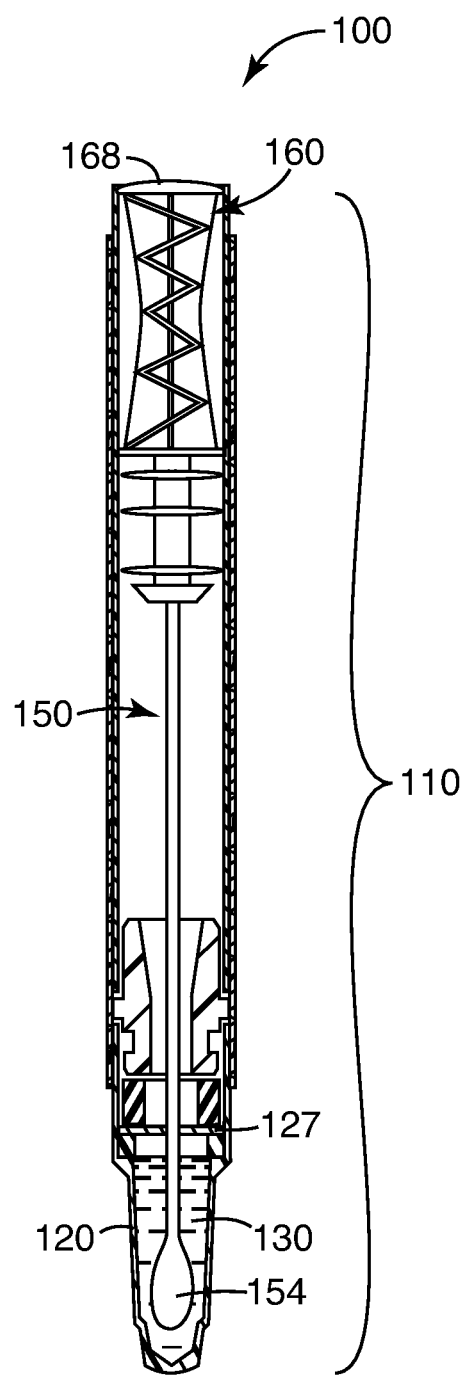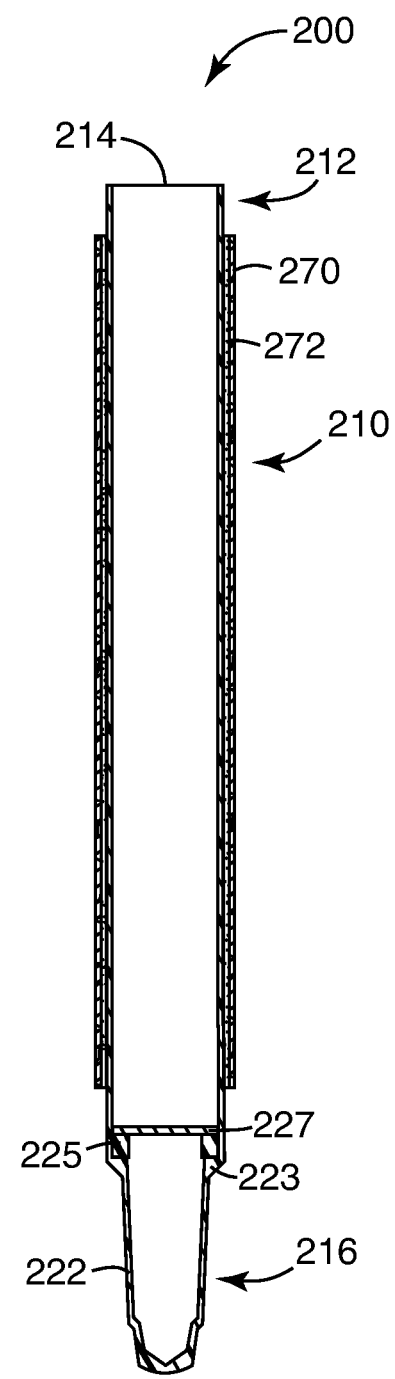
Fig. 1C
Fig. 2

SAMPLING DEVICES AND METHODS OF USE

CROSS REFERENCE TO RELATED APPLICATIONS

This application is a divisional of U.S. patent application Ser. No. 12/992,129, filed Jun. 28, 2011, which is a national stage filing under 35 U.S.C. 371 of PCT/US2009/043748, filed May 13, 2009, which claims priority to United Kingdom Application No. 0808557.3, filed May 13, 2008, the disclosure of which is incorporated by reference in its entirety herein.

BACKGROUND

Environmental sampling is used to monitor critical environments such as food processing areas. Routine sampling and testing can allow quality assurance personnel to detect undesirable materials, such as microorganisms, at a very early stage and take steps to prevent subsequent contamination of equipment and/or products. A variety of tests can be performed to detect the unwanted materials. Examples of such tests include chemical residue (e.g., protein) tests, culture methods, genetic tests (e.g., PCR), immunodiagnostic tests, and bioluminescent tests.

Sample-collection devices typically are used to collect surface samples for environmental tests. Commercially-available sample-collection devices include absorbent devices such as sponges, swabs, and the like. Some of the devices are available in a dry form and may be moistened before use. Alternatively, some devices are available in a premoistened form. Premoistened devices can be advantageous because they do not require the additional step of applying water or other reagents to the collection device and because the moisture helps to loosen or solublize dry materials which may be present on the environmental surface to be analyzed. Such devices may include polymeric materials such as glycerol, polyethylene glycol or polypropylene glycol at a concentration of 10% as a hygroscopic agent.

SUMMARY

It has been found that devices including polymeric materials such as glycerol, polyethylene glycol or polypropylene glycol leave highly undesirable perdurable residues on a surface contacted with such premoistened sample-collection devices and such devices in some cases show incompatible reagents and systems used to detect analytes (e.g., chemical and/or biological analytes) in a collected sample.

It has been surprisingly found that the use of a non-polymeric material 1,2-propanediol shows desirable efficacy in promoting the retention of moisture in pre-moistened sample-collection devices and articles, in particular over periods of extended storage. In addition, sample-collection devices and articles including aqueous solutions comprising 1,2-propanediol have been surprisingly found show desirable efficacy in loosening, solubilizing and/or suspending loosely-bound materials on a surface even after long periods of extended storage, while generally showing favorable compatible with reagents and systems used to detect analytes.

Accordingly, in one aspect, the present disclosure provides a sample-collecting device comprising a shaft and a porous medium coupled to the shaft; the porous medium including an aqueous solution which comprises 1,2-propanediol as a humectant. In certain embodiments the shaft includes a first end and a second end opposite the first end, and wherein the porous medium is proximal the second end of the shaft.

In another aspect, the present disclosure provides a sample-collecting article comprising: a housing with a first end and a second end opposite the first end; and a sample-collecting device disposed therein, wherein the first end of the housing is adapted to receive the sample collecting device. The sample-collecting device housed within the housing comprises a shaft and a porous medium coupled to the shaft; the porous medium including an aqueous solution which comprises 1,2-propanediol as a humectant. In certain embodiments, the shaft includes a first end and a second end opposite the first end, wherein the porous medium is proximal the second end of the shaft and wherein said second end of the shaft is the distal end of the shaft relative to the first end of the housing.

For some article-embodiments, the article further can comprise a cap which is adapted to seal the first end of the housing. In some embodiments, the shaft can be coupled to the cap. In some embodiments, the second end of the housing is a closed end In sample-collecting devices and/or sample-collecting articles, the porous medium can in certain embodiments comprise at least one of fibers, foam, and microreplicated material. In sample-collecting devices and/or sample-collecting articles, the volume of the aqueous solution in certain favorable embodiments can be about 50 microliters to about 1000 microliters.

In sample-collecting devices and/or sample-collecting articles, the concentration of 1,2-propanediol in the aqueous solution can be in some embodiments about 1 weight percent (more particularly about 2 weight percent) to about 10 weight percent.

In particularly favorable embodiments of sample-collecting devices and/or sample collecting articles, the concentration of 1,2-propanediol in the aqueous solution is about 2 weight percent to, but not including 10 weight percent. Some embodiments of devices/articles are particularly advantageous in that some embodiments leave little or no perdurable residue on a surface contacted with said devices/articles while maintaining advantageous desirable efficacy in promoting the retention of moisture in such devices/articles over long term storage. In even more particularly favorable embodiments, the concentration of 1,2-propanediol in the aqueous solution may be about 2 weight percent to about 5 weight percent.

Sample-collecting devices and/or sample-collecting articles described herein may be contained within a moisture-resistant package. Sample-collecting devices and/or sample-collecting articles described herein, may further comprise a reagent. In some embodiments, the reagent can comprise an enzyme substrate for luciferase, phosphatase, or adenylate kinase enzyme activity. In some embodiments, the reagent can be selected from the group consisting of a buffer component, a detergent, a cell lysis reagent, a neutralizing agent, and any combination of two or more of the foregoing.

In sample-collecting devices and/or sample-collecting articles described herein the porous medium may in certain favorable embodiments retain up to 97 weight percent of the aqueous solution after storage at 4 degrees Celsius for 9 months or the porous medium retains up to 89 weight percent of the aqueous solution after storage at 25 degrees Celsius for 12 weeks.

In another aspect, the present disclosure provides a kit; said kit comprising either a sample-collecting device as described herein or a sample-collecting article as described herein. In another aspect, the present disclosure provides A method of detecting an analyte in a sample, the method comprising: providing a sample-collecting device comprising a shaft and a porous medium coupled to the shaft, the porous medium comprising an aqueous solution including 1,2-propanediol as a humectant, the porous medium adapted to collect a sample from a surface;

contacting the sample-collecting device with a surface to obtain a sample; and detecting the analyte. In some embodiments, detecting the analyte can comprise detecting biological material. In some embodiments, the method further can comprise contacting the sample with a lysing agent. In some embodiments, detecting the analyte can comprise detecting a heavy metal.

DEFINITIONS

The use of "including," "comprising," or "having" and variations thereof herein is meant to encompass the items listed thereafter and equivalents thereof as well as additional items. Unless specified or limited otherwise, the term "coupled", "attached", "connected" and variations thereof is used broadly and encompasses both direct and indirect couplings. Further, the term "coupled" is not restricted to physical or mechanical couplings. It is to be understood that other embodiments may be utilized, and structural or logical changes may be made without departing from the scope of the present disclosure. Furthermore, terms such as "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "perdurable detectable residue" means a residue that is detectable by visual or tactile inspection more than 5 minutes after an aqueous liquid comprising a humectant has been contacted with a surface and the surface has been allowed to dry at ambient temperature (i.e., about 18-22° C.) and humidity.

As used herein, "a," "an," "the," "at least one," and "one or more" are used interchangeably. Thus, for example, an article that comprises "a" sample-collecting device can be interpreted to mean that the article includes "one or more" sample-collecting device. Similarly, a method for detecting "an" analyte can be interpreted to mean that the method can involve detecting "one or more" analyte.

The term "and/or" means one or all of the listed elements or a combination of any two or more of the listed elements.

As used herein, the term "or" is generally employed in its sense including "and/or" unless the content clearly dictates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The present invention will be further explained with reference to the drawing figures listed below, where like structure is referenced by like numerals throughout the several views.

FIG. 1C is a partial cross-sectional view of the article of FIG. 1B. The article comprises the exemplary sample-collecting device of FIG. 1A (shown in a side view) disposed in a second position within the exemplary housing of FIG. 1A (shown in a cross-section).

FIG. 2 is a cross-sectional view of the longitudinal axis of one embodiment of an alternative housing according to the present invention.

DETAILED DESCRIPTION

Figure 1A:
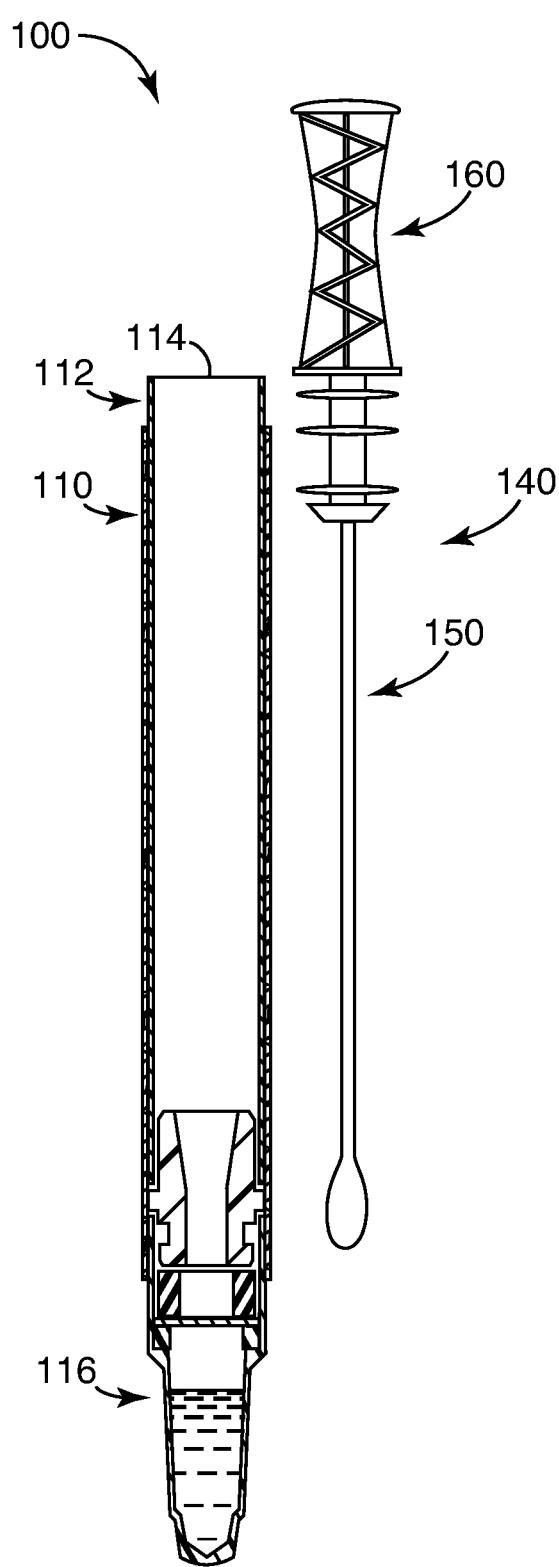
FIG. 1A is a partial cross-sectional view showing a cross-section of the longitudinal axis of one embodiment of a housing and a side view of a sample-collecting device according to the present invention.

During storage, premoistened devices can lose their moisture by evaporation, resulting in a shorter storage shelf life for the device. This moisture loss can be reduced by placing the device in a substantially moisture-resistant package, such as a plastic tube. Minimizing the loss of moisture during storage can add substantial cost to a pre-moistened environmental sampling device. A need exists for a low-cost, premoistened sampling device which can retain moisture for extended periods of time and which does not negatively affect other components of the environmental test.

The recovery of material from a dry environmental surface typically can be improved by using a moist sample-collecting device. Premoistened devices are convenient because the user does not have to prepare and/or provide the moistening solution or add the moistening solution to the device before using it. A disadvantage of premoistened sample-collecting device is that the moisture can evaporate from the device during extended periods of storage (e.g., >6 months at 2-8° C. or >4 weeks at 21° C.).

This invention relates to sample-collecting devices that can be stored for extended periods of time. The invention includes premoistened sample-collecting devices which enhance the collection of material from a surface. The sample collection devices include a porous medium which comprises an aqueous solution comprising 1,2-propanediol as a humectant. 1,2-propanediol facilitates the retention of the aqueous solution in the porous medium during storage of the devices, permitting storage of the devices for extended periods of time. In certain embodiments, the premoistened sample-collecting device may include a detergent and/or a reagent to permeabilize cells. In certain embodiments, the inventive premoistened sample collection device advantageously does not leave a perdurable detectable residue.

The invention further relates to methods wherein the sample-collecting devices are used to test a surface for the presence of an analyte. In addition to helping to retain the moisture in the sample-collecting devices, the aqueous solution comprising 1,2-propanediol as a humectant should be compatible with other components (e.g., chemical reagents and/or proteins such as enzymes or antibodies) used to detect the analyte. In certain preferred embodiments, the sample-collecting device comprising 1,2-propanediol as a humectant does not leave a perdurable detectable residue on the surface.

Sample-collecting devices of the present invention comprise a shaft and a porous medium. The shaft provides a support structure for the porous medium. In some embodiments, the at least a portion of the porous medium can be coupled to the shaft. In some embodiments, the at least a portion of the porous medium can be enclosed by the shaft. An elongated shaft can provide a means to test remote or partially obstructed surfaces, such as crevices or small orifices. Non-limiting examples of suitable sample-collecting devices include swabs and sponges, such as the sponge comprising a handle, as described in U.S. Pat. No. 6,383,804, which is incorporated herein by reference in its entirety.

The shaft of the sample-collecting device can be constructed from various materials such as, for example, wood, plastic, or metal. In some embodiments, the shaft comprises the porous medium (e.g., fibers), which is coated or encased with a material to provide structural support and/or a barrier layer on or around an exterior perimeter of the porous medium. The shaft and the porous medium can be coupled together by a variety of coupling means, including, but not limited to, adhesives, cohesives, magnets, hook-and-loop fasteners, hooks, barbs, clamps, heat sealing, stitches, staples, crimps, welding (e.g., sonic (e.g., ultrasonic) welding), any thermal bonding technique (e.g., heat and/or pressure applied to one or both of the components to be coupled), other suitable coupling means, and combinations thereof. For example, in some embodiments, the porous medium includes fibrous media that can be attached to the shaft by physical entanglement of the fibers on and/or around the surface of the shaft.

The porous medium can be comprised of material that physically and/or chemically collects or binds material present on an environmental surface. Suitable materials for the porous medium include fibers (e.g., cotton, Dacron, rayon, nylon, flocked nylon, polyester, polypropylene, polyethylene, etc.), hydrogels (e.g., agar, agarose, polyacrylamide, etc.), open-cell foams (e.g., polyurethane, cellulose), or microreplicated films such as those described in U.S. Pat. No. 6,867,342, which is incorporated herein by reference in its entirety. In some embodiments, the porous medium comprises hydrophilic materials. In some embodiments, the porous medium comprises hydrophobic materials. In some embodiments, the hydrophobic materials can be treated (e.g., with a coating or a process) to render them relatively hydrophilic. In some embodiments, the porous medium can be a combination of hydrophobic and hydrophilic materials. Of course, it will be recognized that the material used for the porous medium in a device can be selected for compatibility with reagents for the test in which the device will be used.

Sample-collecting devices can be premoistened with an aqueous solution. The solution can be applied to the porous medium by dispensing (e.g., pipetting or spraying) a volume of the solution onto the medium. Alternatively, the porous medium may be dipped into the aqueous solution. The aqueous solution used to premoisten the porous medium can comprise 1,2-propanediol. Alternatively, 1,2-propanediol can be applied to the porous medium after the medium is moistened. In some embodiments, a combination of any of the above techniques can be employed.

Sample-collecting devices can be packaged in moisture-resistant containers. Non-limiting examples of moisture-resistant containers include tubes, bags, pouches, sheaths, and the like. The containers can be constructed from moisture resistant materials, such as plastic (e.g., polypropylene, polyethylene, polyester), glass, or coated paper or fabric. The containers can be sealed (e.g., with a heat seal or an adhesive seal, etc.), which can limit the escape of moisture vapor. In some embodiments, the container may be resealable.

Figure 1B:
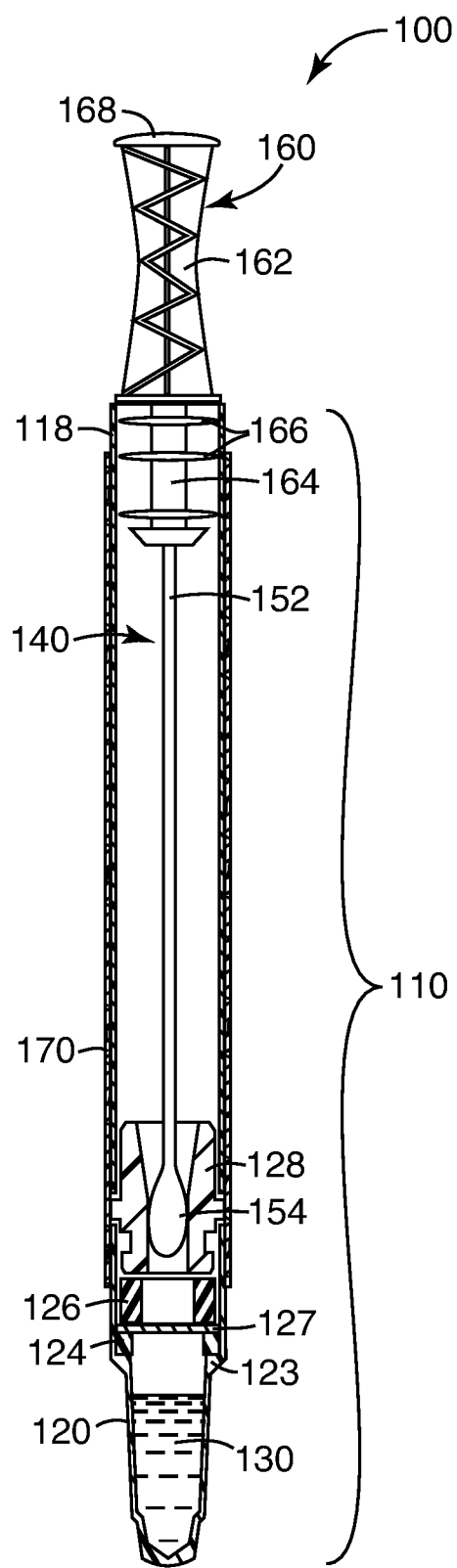
FIG. 1B is a partial cross-sectional view of one embodiment of an article according to the present invention. The article comprises the exemplary sample-collecting device of FIG. 1A (shown in a side view) disposed in a first position within the exemplary housing of FIG. 1A (shown in a cross-section).

Sample-collecting devices can be included in sample-collecting articles which comprise a housing. FIGS. 1A and 1B show a sample-collecting article 100 according to one embodiment for collecting and/or analyzing an environmental sample. The sample-collecting article 100 comprises a housing 110 with a first end 112 and a second end 116. The first end 112 of housing 110 comprises opening 114 into which a sample-collecting device 140 can be inserted for storage and/or use of the sample-collecting article 100. The sample-collecting device 140 comprises a probe 150, which is the portion of the device 140 used to collect the sample, and a cap 160, which includes a handle 162 and a base 164 (see FIG. 1B).

FIG. 1B shows the assembled sample-collecting article 100 before use. The sample-collecting device 140 is in a first position, with the handle 162 of the cap 160 extending outside of the housing 110. In some embodiments, as shown in FIG. 1B, the housing 110 comprises a sleeve 118 and a cuvette 120. The sleeve 118 can be formed (e.g., by injection molding or extrusion) of polymeric materials and may be relatively flexible. The cuvette 120 can be formed from polymeric materials and may be relatively flexible or rigid. In the embodiment illustrated in FIG. 1B, the cuvette 120 comprises a flange 123. The cuvette 120 can be a variety of geometric shapes, such as cubic, cuboid, cylindrical, conical, frusto-conical, other suitable geometric shapes, and combinations thereof. Preferably, the walls of the cuvette 120 can be configured to allow the passage of light (e.g., visible light) into and/or out of the cuvette 120.

The cuvette 120 can be coupled to the sleeve 118 using a collar 128. The collar 128 can be made from a variety of materials (e.g. molded plastic) and at least a portion of the collar 128 can be dimensioned to be received in the sleeve 118 and the cuvette 120 to couple the sleeve 118 and the cuvette 120 together. A skilled person will recognize other means by which the sleeve 118 and cuvette 120 can be coupled together. A pot 126 is positioned adjacent the collar 128, and a frangible barrier 127 is coupled to the pot 126. The frangible barrier 127 can be coupled to either end of the pot 126. In the embodiment shown in FIG. 1, the frangible barrier 127 is located on the end of the pot 126 proximal the cuvette 120. The pot 126 can be made from a number of materials (e.g. molded or extruded plastic). The frangible barrier 127 can be made from a water-resistant material, such as plastic film, metal foil, or a metal-coated plastic film. When assembled, the collar 128 urges the pot 126 against a sealing member 124 (e.g., an O-ring), which contacts the flange 123. The sealing member 124 and the frangible barrier 127 can together form a water-resistant barrier to prevent the unintended movement of reagent solution 130 from the cuvette 120. The sealing member 124 can be formed from a relatively flexible, malleable material, such as silicone or butyl rubber. An optional lamina 170 can hold the cuvette 120 firmly together with the sleeve 118. The lamina 170 can be made from paper or a plastic film, for example, and may be used as a label.

Positioned in the housing 110 is the sample-collecting device 140. The sample-collecting device 140 comprises a shaft 152 and porous medium 154. The shaft 152 can be constructed from a variety of materials, such as wood, plastic, metal, or combinations thereof. In some embodiments, the shaft 152 can be flexible to probe tortuous spaces. In other embodiments, the shaft 152 can be relatively inflexible, so that force can be applied to the shaft 152 to help obtain a sample. As shown in FIG. 1B, the shaft 152 is adapted to be inserted into the base 164 of cap 160. In some embodiments, the shaft 152 can be hollow and/or can be connected to a liquid reservoir, as described in U.S. Pat. Nos. 4,978,504 and 5,879,635, which are incorporated herein by reference in their entirety. As mentioned above, the porous medium 154 can comprise, but is not limited to, fibers, hydrogels, open-cell foams, microreplicated materials, and combinations thereof. The base 164 of the cap 160 comprises at least one sealing member 166, which is adapted to hold the cap 160 firmly in sleeve 118 and/or to seal (e.g. hermetically seal) the interior of the housing 110 when the cap 160 is assembled to the housing 110. The cap 160 can be made of plastic material, for example, by an injection-molding process.

During use, the sample-collecting device 140 can be grasped by the handle 162 and removed from the housing 110 to sample a surface. After sampling a surface, the probe 150 can be reinserted into the housing 110 and a distal end 168 of the cap 160 can be pressed to move the cap into a second position (FIG. 1C). As the cap 160 moves to the second position in the housing 110, the frangible barrier 127 is punctured, and the porous medium 154 moves into the cuvette 120. In this position, the porous medium 154 can contact the reagent solution 130 to facilitate the detection of an analyte.

FIG. 2 illustrates a sample-collecting article 200 according to another embodiment of the present disclosure, wherein like numerals refer to like elements. As shown in FIG. 2, the sample-collecting article 200 includes a housing 210, and a lamina 270, which can be coupled to the housing 210 by an adhesive layer 272.

In this embodiment, the one-piece housing 210 comprises a first end 212 and a second end 216. The first end 212 comprises an opening 214 into which a sample-collecting device (e.g., the sample collecting device 140) can be inserted. The second end 216 comprises a flange 223 and a cuvette portion 222. The housing 210 can be constructed from a variety of materials, such as glass or plastic polymers (e.g., polypropylene, polystyrene, polycarbonate). A frangible barrier can be positioned against the flange 223. In this embodiment, the frangible barrier 227 is coupled to the flange 223 by adhesive 225. A skilled person will recognize a variety of other means by which the frangible barrier 227 could be secured in the proper position adjacent the cuvette portion 222 of the housing 210. In one embodiment (not shown), a pot comprising a frangible barrier (as shown in FIG. 1) can be coupled to the flange (e.g., by an adhesive) to secure the frangible barrier in place.

The sample-collecting article 200 can further include a sample-collecting device, such as the sample-collecting device 140 illustrated in FIGS. 1A-1C and described above, to puncture the frangible barrier 227 and move a porous medium into the cuvette portion 222 of the housing 210.

Figure 3:
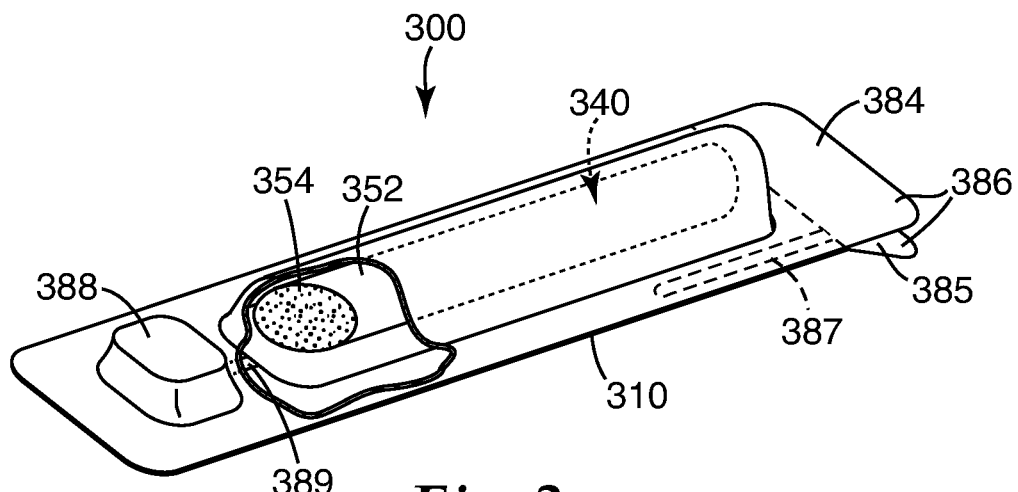
FIG. 3 is a partially exploded view of one embodiment of an alternative sample-collecting device according to the present invention.

FIG. 3 illustrates a sample-collecting article 300 according to another embodiment of the present disclosure, wherein like numerals refer to like elements. The sample-collecting article 300 comprises a sample-collecting device 340 and a housing 310. The sample-collecting device 340 comprises a porous medium 354, which is partially encased by shaft 352. An exposed portion of the porous medium 354, is contacted with a surface to obtain a sample while the sample-collecting device 340 is grasped by the shaft 352. The shaft 352 can be constructed from a variety of materials including, for example, plastic, glass, metal. In certain alternative embodiments, the porous medium 354 integrally comprises (e.g., as a coating) the shaft 352. The porous medium can be constructed from a variety of absorbent materials, such as foams, sponge, cotton, nylon, or cellulose. Alternatively, the porous medium can be constructed from a microstructured film or a laminate of microstructured films, as described in U.S. Pat. No. 6,867,342. The porous medium 354 can be premoistened with an aqueous solution.

The sample collecting device 340 can be sealed in the housing 310, which can be moisture-resistant. FIG. 3 shows the housing 310 can include two or more lamina, such as a top layer 384 and a bottom layer 385. The lamina can be constructed of a variety of materials, including, but not limited to, plastic film, metal foil, metalized plastic film, coated paper, other suitable materials, and combinations thereof. The lamina can be coupled together by adhesives and/or by heat-sealing, for example. The sample-collecting article 300 further comprises a reagent chamber 388 and a seal region 389. The lamina of the housing 310 are less-securely adhered (e.g., having a thinner layer of adhesive) in the seal region 389 than in other portions of the housing 310.

In use, the operator grasps tabs 386 to separate the top layer 384 and the bottom layer 385 along a seam 387. The sample-collecting device 340 is grasped by shaft 352 to remove the sample-collecting device 340 from the housing 310. The porous medium 354 is contacted with a surface to obtain a sample and the sample-collecting device 340 is returned to the housing 310 with the porous medium 354 adjacent the seal region 389. Force applied to the reagent chamber 388 (e.g., by squeezing the chamber) causes the seal region 389 to delaminate, allowing a reagent solution to flow out of the reagent chamber 388 and contact the porous medium 354 of the sample-collecting device 340. In some embodiments, the reagent chamber 388 may contain reagents, such as a protein error indicator (e.g., tetrabromophenol-phthalein ethylester and tetrabromophenol blue), which can react with an analyte, such as protein, to detect the presence of the analyte in the sample. Protein error indicators are described in U.S. Pat. No. 4,013,416, which is incorporated herein by reference in its entirety.

Sample-collecting articles of the present disclosure can be packaged in moisture-resistant containers. Non-limiting examples of moisture-resistant containers include tubes, bags, pouches, sheaths, and the like. The containers can be constructed from moisture resistant materials, such as plastic (e.g., polypropylene, polyethylene, polyester), glass, or coated paper or fabric. The containers can be sealed with a heat seal or an adhesive seal, for example, to limit the escape of moisture vapor. In some embodiments, the container may be resealable. In some embodiments, the sample-collecting articles may be sterilized using gamma irradiation, for example.

Sample-collecting articles can comprise a reagent. The reagent can facilitate detection of an analyte in a sample.

Suitable reagents for sample-collecting articles include a buffer component, a detergent, a cell lysis reagent, a neutralizing agent, an enzyme activity (e.g., luciferase enzyme activity, phosphatase enzyme activity, or adenylate kinase enzyme activity), an enzyme substrate (e.g., a substrate for luciferase enzyme activity, a substrate for phosphatase enzyme activity, or a substrate for adenylate kinase enzyme activity), and any combination of two or more of the foregoing reagents.

In favorably embodiments the porous medium retains up to 97 weight percent of the aqueous solution after storage at 4 degrees Celsius for 9 months or the porous medium retains up to 89 weight percent of the aqueous solution after storage at 25 degrees Celsius for 12 weeks.

Figure 4:
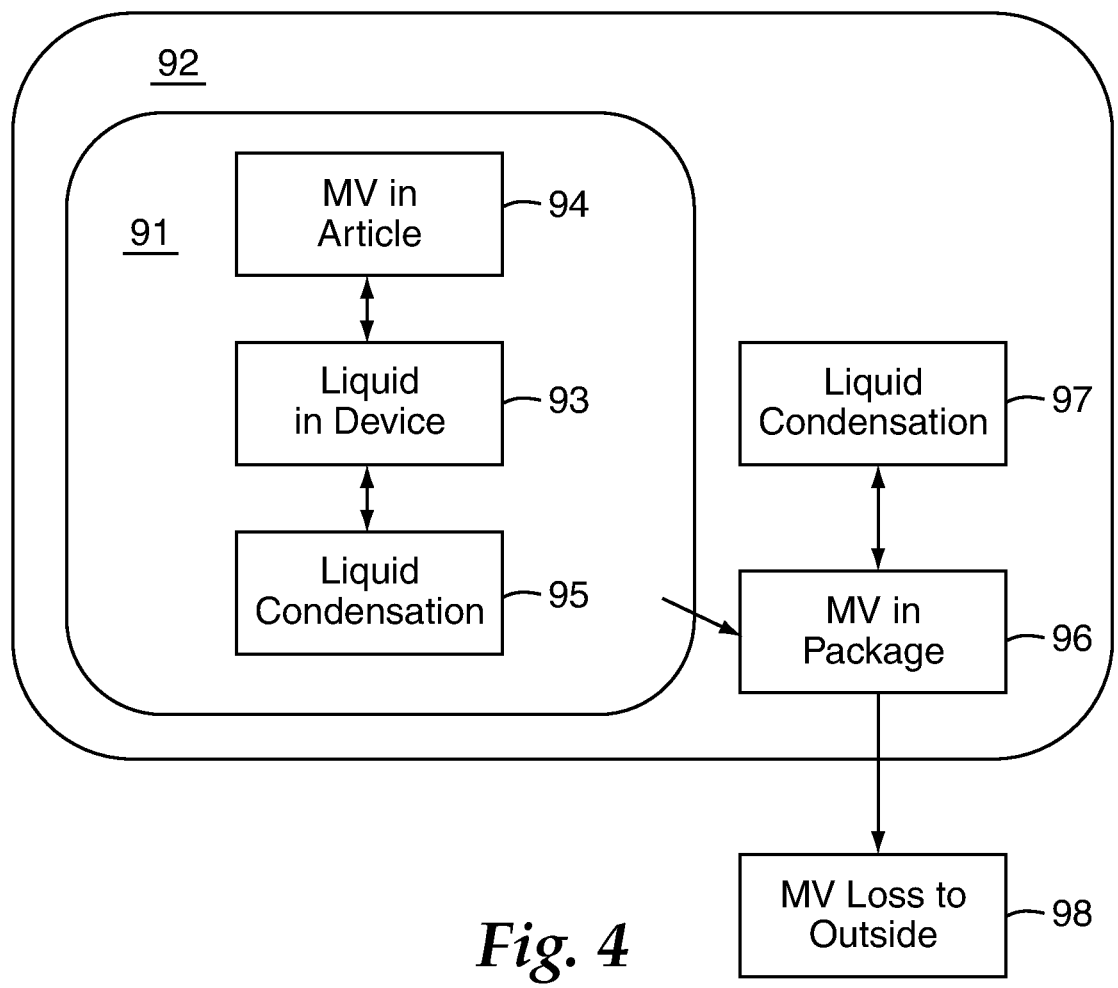
FIG. 4 is a block diagram of the movement of moisture vapor within an article comprising a premoistened sample-collecting device.

FIG. 4. shows a block diagram illustrating moisture vapor (MV) transfer to and from a premoistened sample-collecting device contained within two enclosures. Block 93 represents the liquid contained on and/or in a premoistened sample-collecting device. In this embodiment, the sample-collecting device is present within a primary container 91, such as a housing or a tube, which is present in a secondary container 92, such as a pouch or a bottle. If the relative humidity of the air within the primary container 91 is low, liquid from the device may evaporate (as shown in block 94) until the air becomes saturated with MV. Some of the MV in the primary container 91 may condense into liquid, as shown in block 95. Alternatively, some of the MV in the primary container 91 may diffuse out of the primary container 91 and into the secondary container 92, as shown in block 96. If the relative humidity of the air in the secondary container 92 is low, MV may diffuse from the primary container 91 until the air in the secondary container 92 becomes saturated with MV. Some of the MV in the secondary container 92 may condense into liquid, as shown in block 97. Alternatively, some of the MV in the secondary container 92 may diffuse to the outside, as shown in block 98. A skilled person will recognize that all of these illustrated movements of moisture vapor can be affected by the temperatures and relative humidity present within each container and within the outside environment outside the containers 91, 92. The inventive use of 1,2-propanediol as a humectant as disclosed herein can be used to prolong the moisture retention by the sample-collecting device, relative to devices which do not contain a humectant. For example, the Device in block 93 of FIG. 4 can include any of the sample-collecting devices 140, 340 described above, the primary container 91 can include any of the housings 110, 210, described above, and the secondary container 92 can include any of the sample-collecting articles 100, 200, 300 described above.

The porous medium of a sample-collecting device may be moistened with an aqueous solution. In some embodiments, the sample-collecting device is premoistened before placing and/or storing the device in an article or in packaging. The moistening liquid can include one or more reagents. The reagents can be useful for a variety of purposes including, for example, retention of moisture in the porous medium, lysing biological cells, loosening or dissolving sample material, and/or detecting an analyte in a sample. The reagents may be added to the porous medium before applying the moistening liquid. Alternatively, reagents may be suspended and/or dissolved in the moistening liquid before applying the liquid to the porous medium.

The volume of moistening liquid added to the porous medium can be adjusted according to several factors including, for example, the liquid capacity of the medium, the length of time the device will be stored, the volume and the moisture permeability of the primary container in which the device will be stored, and the amount of 1,2-propanediol added to the moistening solution. In general, a larger volume of moistening solution will be added to devices with larger, more absorbent porous medium. In some embodiments, the porous medium of a sample-collecting device will comprise about 50 to about 1,000 microliters of liquid. In certain embodiments, the device comprises about 50 microliters, about 100 microliters, about 150 microliters, about 200 microliters, about 250 microliters, about 300 microliters, about 500 microliters, about 600 microliters, about 700 microliters, about 800 microliters, about 900 microliters, or about 1,000 microliters.

The use of 1,2-propanediol in conjunction with the moistening liquid, favorably prolongs the retention of moisture in the porous medium. Preferably, 1,2-propanediol does not substantially inhibit the activities (e.g., interfere with an enzyme activity or the ability of a protein to recognize and/or bind to another molecule) of proteins (e.g., enzymes, antibodies), if the protein is present in the sample or the test device. In particular embodiments, 2-propanediol-containing solution does not leave a perdurable detectable residue on the surface which is contacted with a sample-collecting device comprising a humectant-containing solution. A "perdurable detectable residue", as used herein, refers to a liquid or solid residue which does not become substantially invisible upon evaporation of the liquid solvent and/or leaves a perceptible tactile effect, such as a perceptibly sticky or oily feel. A visual test for residue can be done, for example, by rubbing a sample-collecting device comprising a humectant-containing solution on about 1-10 $cm^2$ of a clean, dry surface such as a stainless steel coupon, allowing the liquid residue to evaporate for about 5 minutes at ambient temperature, and observing the surface for any remaining moisture. A tactile test for residue can be done, for example, by rubbing a sample-collecting device comprising a humectant-containing solution on about 1-4 $cm^2$ of a clean, dry surface such as a stainless steel coupon, allowing the liquid residue to evaporate for about 5 minutes at ambient temperature, and rubbing the surface with a clean, dry finger to observe any sticky- or oily-feeling residue.

1,2-propanediol can be dissolved and/or diluted in an aqueous solution (e.g., a buffer or sterile deionized water), for example, at a appropriate concentration of 1%, 2%, 3%, 5%, 7.5%, etc weight:volume (w/v) and placed in the porous medium of a sample-collecting device. The concentration of 1,2-propanediol in the aqueous solution may be about 1 weight percent to about 10 weight percent, or about 2 weight percent to about 10 weight percent. 1,2-propanediol, present at concentrations from about 2 weight percent to, but not including, 10 weight percent in the aqueous solution, has been found particularly suitable for prolonging the retention of moisture in a sample-collecting device while leaving little or no perdurable detectable residue on a surface. 1,2-propanediol, present at a concentrations of about 2 weight percent to about 5 weight percent in the aqueous solution are even more advantageous.

Cell lysis reagents can be added to the moistening liquid to help permeabilize biological cells and facilitate the detection of an analyte associated with the cells. The detection of intracellular analytes (e.g., nucleic acids, proteins, oligopeptides, and small molecules such as ATP) and cell wall-associated or cell-membrane associated molecules (e.g., polysaccharides and proteins) can be facilitated by cell lysis reagents. Preferably, the cell lysis reagent does not substantially inhibit the activities (e.g., interfere with an enzyme activity or the ability of a protein to recognize and/or bind to another molecule) of proteins (e.g., enzymes, antibodies), if the protein is present in the sample or the test device. Cell lysis reagents and their effective concentrations are known in the art. Examples of cell lysis agents include detergents (e.g., TRITON X-100), biocides (e.g., chlorhexidine gluconate, benzalkonium chloride), enzymes (e.g., phospholipases, lysozyme, lysostaphin), and cytolytic peptides (e.g., phylloxin).

Detergents can be added to the moistening liquid to help loosen and/or solublize material that is present on a surface to be tested with a sample-collecting device. The detection of analytes can be facilitated by detergents. Preferably, the detergent does not substantially inhibit the activities (e.g., interfere with an enzyme activity or the ability of a protein to recognize and/or bind to another molecule) of proteins (e.g., enzymes, antibodies), if the protein is present in the sample or the test device. Suitable detergents include, for example TRITON X-100. The detergents can be used at relatively low concentrations, such as the low concentrations that are typically used in the art.

In some embodiments, the moistening solution can contain a neutralizing agent. The neutralizing agent can function to neutralize or inactivate a component of the environmental sample that could interfere with a detection system. In some embodiments, the neutralizing agent can be a buffer component, to control the pH within a desirable range (e.g., about pH 5-9, about pH 6-8, about pH 6.5-7.5, about pH 7, about pH 8, at a low pH such as <6, or at a high pH such as >9). In some embodiments, the neutralizing agent can comprise a chelating agent such as sodium EDTA. In some embodiments, the neutralizing agent can comprise a protease inhibitor (e.g., leupeptin, aprotinin) or nonspecific protein (e.g. bovine serum albumin) to inhibit or reduce protease activity in the sample that could interfere with a detection system involving a protein reagent (e.g., an antibody).

In some embodiments, several reagents can be included in the moistening solution. For example, the moistening solution can contain as humectant 1,2-propanediol and a cell lysis reagent such as chlorhexidine gluconate. In another embodiment, the moistening solution can contain as humectant 1,2-propanediol and a detergent such as TRITON X-100. In another embodiment, the moistening solution can contain as humectant 1,2-propanediol, a cell lysis reagent such as chlorhexidine gluconate, and a detergent such as TRITON X-100.

Sample-collecting devices of the present invention can be used to collect a variety of samples. Non-limiting examples of suitable samples include solids, semi-solids, gelatinous materials, particulate suspensions, solutions, liquids, and combinations thereof. Samples can be collected by contacting the porous medium with the material or surface to be sampled. Samples can be collected from relatively hard surfaces, such as plastics, metals, minerals, or composite materials. Samples can be collected from relatively soft surfaces, such as plant or animal tissue (e.g., skin or mucous membranes). Samples can be collected from liquid interfaces.

The terms "surface" or "environmental surface" generally refer to any surface from which a sample can be collected. The surface to be tested can be present in a variety of locations, including, but not limited to, healthcare facilities (e.g., hospitals, doctor offices, etc.), daycare facilities, schools, swimming pools, restrooms (e.g., commodes, sinks, shower stalls), locker rooms, fitness facilities (e.g., group fitness studios, gyms, etc.), long term care facilities (e.g., nursing homes), food processing plants, homes, offices, food service facilities, hotels, transportation vehicles (e.g., automobiles, buses, trains, airplanes, boats, cruise ships, etc.), etc. Examples of surfaces can include, but are not limited to, walls (including doors), floors, ceilings, drains, refrigeration systems, ducts (e.g., air ducts), vents, toilet seats, handles, doorknobs, handrails, bedrails (e.g., in a hospital), countertops, tabletops, eating surfaces (e.g., trays, dishes, etc.), working surfaces, equipment surfaces, clothing, etc., and combinations thereof.

Devices and methods of the present invention can be particularly useful for environmental monitoring; for example in food-, water-, or pharmaceutical-, or medical device-processing environments. Sample-collecting devices comprising reagents such as a detergent can facilitate the collection of material that may be loosely adhered to a surface.

Moistened sample-collecting devices, articles, and methods of the present invention can be used to detect a variety of analytes. In some embodiments, they can be used to detect biological cells in clinical or environmental samples. The biological cells may be detected directly, for example by performing a genetic assay (e.g., PCR), an immunoassay, or by culturing microorganisms present on the sample-collecting device. Microorganisms of interest include prokaryotic and eukaryotic organisms, particularly Gram positive bacteria, Gram negative bacteria, fungi, protozoa, *mycoplasma*, yeast, viruses, and even lipid-enveloped viruses. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Listeria* spp., *Vibrio* spp., *Corynebacteria* spp., as well as herpes virus, *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis, Streptococcus pneumoniae, S. agalactiae, S. pyogenes, Enterococcus faecalis*, Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracis, Pseudomonas aeruginosa, Escherichia coli, Aspergillus niger, A. fumigatus, A. clavatus, Fusarium solani, F. oxysporum, F. chlamydosporum, Listeria monocytogenes, Listeria ivanovii, Vibrio cholera, V. parahemolyticus, Salmonella cholerasuis, S. typhi, S. typhimurium, Candida albicans, C. glabrata, C. krusei, Enterobacter sakazakii, E. coli* O157 and multiple drug resistant Gram negative rods (MDR).

The sample-collecting devices, articles, and methods can be used to detect biomolecules (e.g., proteins, polysaccharides, nucleic acids, nucleotides such as ATP, GTP, NAD, and NADP) that are indicative of biological cells in a clinical or environmental sample. Gram positive and Gram negative bacteria are of particular interest. Of even more interest are Gram positive bacteria, such as *Staphylococcus aureus*. Typically, these can be detected by detecting the presence of a cell-wall component characteristic of the bacteria, such as a cell-wall protein. Also, of particular interest are antibiotic resistant microbes including MRSA, VRSA, VISA, VRE, and MDR. Typically, these can be detected by additionally detecting the presence of an internal cell component, such as a membrane protein, transport protein, enzyme, etc., responsible for antibiotic resistance.

In some embodiments, the sample-collecting devices, articles, and methods can be used to detect chemicals in an environmental sample. For example, the devices or articles could be used to collect a sample for the analysis of heavy metals, such as lead or mercury. Lead salts, such as lead acetate can be reacted with potassium chromate or potassium iodide to form an insoluble precipitate, which can be measured gravimetrically. In some embodiments, heavy metals such as lead can be measured by X-ray fluorescence.

The sample-collecting devices and articles described herein can be used in a variety of methods to detect analytes in a sample. After collecting the samples, analytes can be eluted from the porous medium by various means that are known in the art, such as immersing the porous medium in tube containing a buffered solution and vortexing the tube to release material from the porous medium. The analytes may then be detected directly in the solution or they may be detected after a concentration process, such as centrifugation (particulate analytes), filtration (particulate analytes), or chromatography (soluble analytes).

The analytes that are released from the porous medium can be detected by various methods that are well known in the art, such as culture methods (for viable microorganisms), genetic methods (e.g., amplification, hybridization, or labeling techniques), immunoassay methods (e.g., ELISA, radioimmunoassay, immunochromatography, affinity chromatography), or chemical methods (e.g., protein assay, ATP assay, lead assay).

The detection of some analytes can involve a chromogenic (or colorimetric) assay. For example, some ELISA tests include the use of a phosphatase enzyme activity and a chromogenic substrate (o-nitrophenylphosphate) which, when hydrolyzed by phosphatase, produces a yellow compound (o-nitrophenol). Certain protein assays include the use of cuprous ions, which are reduced to cupric ions that subsequently are chelated by bicinchoninic acid to form a purple compound. Thus, the presence of the analyte in the sample leads to a color change which can be detected either visually or by an instrument, such as a spectrophotometer. Certain protein assays include the use of protein error indicators, which are pH indicators that change color in the presence of protein.

The detection of some analytes can involve a lumigenic (or lumimetric) assay. For example, some ATP tests include the use of a luciferase enzyme activity and a substrate (luciferin) which, upon reaction with ATP and oxygen results in the emission of light at about 562 nm. Thus, the presence of ATP in the sample leads to light emission which can be detected by an instrument, such as a luminometer. The detection of ATP from live cells in a sample can be enhanced by using a cell lysis reagent, such as chlorhexidine, which can permeabilize the cells to facilitate the interaction of the luciferin and luciferase with the cellular ATP.

EXAMPLES

Objects and advantages of this invention are further illustrated by the following examples, but the particular materials and amounts thereof recited in these examples, as well as other conditions and details, should not be construed to unduly limit this invention.

All parts, percentages, ratios, etc. in the examples are by weight, unless noted otherwise. Solvents and other reagents used were obtained from Sigma-Aldrich Chemical Company (St. Louis, Mo.), unless otherwise noted. TRITON X-100 was obtained from NBS Biologicals (Cambridgeshire, UK). Purified water, obtained from a MILLI-Q water system (Millipore, Billerica, Mass.), was used to prepare all aqueous solutions, unless otherwise noted.

Example 1

Moisture Retention by Sampling Devices During Extended Storage

Rapid Cleanliness Test swab sampling devices, sold under the trade name CLEAN-TRACE, were obtained from 3M Health Care (Bridgend, UK). Sterile Dacron swabs were obtained from Puritan Medical Products Company (Guilford, Me.). Foil pouches (160 mm (w)×270 mm (1) heat-sealable PET/foil/LDPE laminate pouches) were obtained from Westfield Medical Ltd. (Bath, UK). The analytical balance (model GR-300) was obtained from A&D Mercury Pty., (Thebarton, South Australia)

The swabs were removed from the CLEAN-TRACE devices and replaced with dry, sterile Dacron swabs. Half of the replacement swabs were dipped in solution I (see Table 1) for 20 seconds, tapped on the edge of a sterilin container 5 times (to remove excess swabbing solution), and the swabs were weighed before each CLEAN-TRACE tube was reassembled with a moistened swab. The remaining replacement swabs were similarly moistened with solution II (Table 1), weighed, and reassembled in the tubes.

TABLE 1

Composition of the solutions used to moisten the swabs.

| Solution | Composition |
|---|---|
| I | Triton X-100 - 1.62 g/L |
|   | Chlorhexidine - 3.53 g/L |
| II | Triton X-100 - 1.62 g/L |
|    | Chlorhexidine - 3.53 g/L |
|    | Propane 1,2-diol ("PD") - as specified as Table 2 |

The initial weight ($T_0$) of each moistened swab was recorded. The reassembled tubes were placed into individual plastic pouches, which were heat-sealed. Care was taken to minimize the amount of air sealed in each pouch. The pouches were divided into two groups. One group was placed into a refrigerator which was held at a temperature of 4±3 degrees Celsius. The other group was placed into a chamber which was held at 25±1 degree Celsius. Sets of ten replicate tubes were removed from each chamber at each specified time point, the tubes were removed from the pouch and weighed, and the weights were recorded. The data are presented in Table 2.

TABLE 2

Moisture loss during storage at various temperatures. Swabs were prepared and packagedas described in Example 1. Each data point represents the average of 30 separate devices per condition at each time point. The numbers represent the difference between the mass of the swab at $T_0$ and the mass of the swab at the indicated time point.

|  | Solution I (Control) | Solution II (2 (w/v) % PD) | Solution II (5 (w/v) % PD) |
|---|---|---|---|
| 3 Months (4° C.) | −11.9 ± 0.003 | −3.57 ± 0.004 | −3.72 ± 0.004 |
| 6 Months (4° C.) | −9.58 ± 4.56 | −9.15 ± 4.57 | −4.52 ± 4.01 |
| 9 Months (4° C.) | −13.51 ± 4.39 | −10.61 ± 3.55 | −3.55 ± 3.53 |
| 4 weeks (25° C.) | −24.51 ± 6.44 | −7.04 ± 3.73 | −6.37 ± 1.35 |
| 8 weeks (25° C.) | −32.40 ± 7.14 | −14.29 ± 0.56 | −17.77 ± 3.91 |
| 12 weeks (25° C.) | −49.13 ± 5.70 | −31.32 ± 4.67 | −18.32 ± 3.50 |

Example 2

Effect of a 1,2-Propanediol-Containing Solution on the Background Reading (Negative Control) of a Colorimetric Protein Assay PRO-TECT Medical devices, PRO-TECT foam swabs, and the PRO-LITE reader were obtained from 3M Health Care (Bridgend, UK). PRO-TECT devices are used in a colorimetric test to detect protein residue based on a Biuret reaction (e.g., Bicinchoninic acid/CuSO4) that is sensitive to the presence of protein in a sample. A standard laboratory heating block was used for 37-degree incubation procedures.

Ten foam and ten polyester swabs were dipped in swab Solution I (Example 1) for 15 seconds. Another 10 swabs of each type were dipped in swab Solution II (see Example 1) with 5% PG for 15 seconds. All swabs were labeled and then reassembled in PRO-TECT devices. Five devices with each swab type were used as blank controls with nothing on the bud.

PRO-TECT devices were activated in 30 second intervals and incubated at the temperature specified in Table 3. For the foam swabs, the standard PRO-TECT incubation assay was used (10 min at 20° C.). Devices were incubated in the laboratory at ambient temperature. PRO-TECT M swabs were incubated using the heating block at 37° C. for 45 minutes. The color change was observed visually and recorded according to the manufacturer's instructions. After visual analysis, the absorbance was measured in the PRO-LITE reader according to the manufacturer's instructions. Visual results and PRO-LITE readings were recorded and the data for each swab type are presented in Table 3 and Table 4, respectively. The results show that the 1,2-propanediol did not significantly alter the background (no protein) readings of the protein assays conducted with each type of read-out (i.e., visual and instrumental read-outs).

TABLE 3

Effect of 5% 1,2-propanediol on a biuret reaction. Polyester swabs were dipped in the Solution I or Solution II before performing the PRO-TECT protein assay according to the manufacturer's instructions.

| Swab number | Solution I | | Solution II (5 (w/v) % PD) | |
|---|---|---|---|---|
| | Abs. (RCU) | Visual Reading | Abs. (RCU) | Visual Reading |
| 1 | 174 | 1 | 204 | 1 |
| 2 | 213 | 1 | 189 | 1 |
| 3 | 200 | 1 | 183 | 1 |
| 4 | 196 | 1 | 199 | 1 |
| 5 | 188 | 1 | 208 | 1 |
| 6 | 174 | 1 | 164 | 1 |
| 7 | 211 | 1 | 197 | 1 |
| 8 | 199 | 1 | 178 | 1 |
| 9 | 199 | 1 | 212 | 1 |
| 10 | 204 | 1 | 191 | 1 |
| Ave. RCU (±S.D.) | 196 ± 14 | | 192 ± 15 | |

TABLE 4

Effect of 5% 1,2-propanediol on a biuret reaction. Foam swabs were dipped in the Solution I or Solution II before performing the PRO-TECT M protein assay according to the manufacturer's instructions.

| Swab number | Solution I | | Solution II (5 (w/v) % PD) | |
|---|---|---|---|---|
| | Abs. (RCU) | Visual Reading | Abs. (RCU) | Visual Reading |
| 1 | 376 | 2 | 339 | 2/3 |
| 2 | 343 | 1/2 | 375 | 1/2 |
| 3 | 360 | 2 | 367 | 1/2 |
| 4 | 391 | 2 | 360 | 1/2 |
| 5 | 375 | 1/2 | 397 | 1/2 |
| 6 | 378 | 1/2 | 373 | 1/2 |
| 7 | 341 | 2 | 367 | 2/3 |
| 8 | 370 | 1/2 | 393 | 1/2 |
| 9 | 349 | 2 | 379 | 1/2 |
| 10 | 365 | 2 | 363 | 2/3 |
| Ave. RCU (±S.D.) | 365 ± 16 | | 371 ± 17 | |

Example 3

Effect of a 1,2-Propanediol-Containing Solution on the Detection of ATP in a Sample Preparation of Test Devices Rapid Cleanliness Test swab sampling devices, sold under the trade name CLEAN-TRACE, were obtained from 3M Health Care (Bridgend, UK). Sterile Dacron swabs were obtained from Puritan Medical Products Company (Guilford, Me.). Foil pouches (160 mm (w)×270 mm (1) heat-sealable PET/foil/LDPE laminate pouches) were obtained from Westfield Medical Ltd. (Bath, UK).

The swabs were removed from the CLEAN-TRACE devices and replaced with dry, sterile Dacron swabs. One-third of the replacement swabs were dipped in solution I (see Table 1) for 20 seconds, tapped on the edge of a sterilin container 5 times (to remove excess swabbing solution), and the CLEAN-TRACE tube was reassembled with the moistened swab. One-third of the remaining replacement swabs were similarly moistened with solution II (Table 1) containing 2% (w/v) 1,2-propanediol and reassembled in the tubes. The remaining one-third were similarly moistened with solution II (Table 1) containing 5% (w/v) 1,2-propanediol and reassembled in the tubes. The reassembled devices were sealed in pouches containing 10 devices per pouch and stored at 4 degrees Celsius for 24 hours.

Activity Test

An ATP stock solution was prepared by reconstituting freeze-dried ATP with 500 microliters of autoclaved R.O. water to a working strength of $1 \times 10^7$M. A 10-microliter aliquot of the ATP working solution was pipetted onto the middle of the bud of the test devices prepared for this Example (see above).

Individual devices were activated by plunging the handle of the swab into the test devices, thereby breaking the barrier and exposing the swab bud to the reagent solution containing luciferin. The tubes were then shaken for 20 seconds at speed 7 on the wrist action shaker (Stuart Scientific, Staffordshire, England) and the device was read device in a UNI-LITE luminometer (3M Healthcare, Bridgend, U.K.). Twenty replicate swabs were tested at each time point for each swab solution. Background readings (negative controls) were run at each time point by activating devices, containing one of the Solutions (I, IIa, or IIb), which was not spiked with the ATP solution. Ten devices were used for each negative control condition at each time point. The results are shown in Table 5. The data indicate that the solutions containing 1,2-propanediol did not significantly affect the qualitative or quantitative detection of ATP on the swabs.

TABLE 5

Activity of CLEAN-TRACE devices with swabs dipped in swabbing solution containing 0%, 2% and 5% PG, after storage at 4° C. Each data point represents the average of the twenty swabs that were tested. Negative controls consistently averaged 18.9 ± 2.3, 18.2 ± 3.6, 19.3 ± 2.9 relative light units (RLUs), for swabs premoistened with solutions I, IIa, and IIb, respectively.

| Time (Months) | Solution I | Solution IIa (2 (w/v) % PG) | Solution IIb (5 (w/v) % PG) |
|---|---|---|---|
| 3 | 9720 | 9376 | 8919 |
| 5 | 9517 | 9027 | 9065 |
| 6 | 9311 | 8686 | 8558 |
| 7 | 8805 | 8531 | 8499 |
| 8 | 8462 | 8356 | 8428 |
| 9 | 8939 | 8417 | 8625 |

Example 4

Assessment of Perdurable Detectable Residue Left by 1,2-Propanediol-Containing Solutions Used for Premoistening a Sample-Collecting Device Preparation of Devices CLEAN-TRACE devices were obtained from 3M Health Care (St. Paul, Minn.). The premoistened swabs were removed from the devices and replaces with dry Dacron swabs. The dry swabs were premoistened by dipping them in the indicated solution for 20 seconds. The swab was removed from solution and tapped on side of sterilin container for 5 seconds to remove excess moisture. One-third of the swabs were dipped in Solution I (see Example 1) and replaced in the CLEAN-TRACE devices (this group of devices was the control group). One-third of the swabs were dipped in Solution II containing 2% (w/v) 1,2-propanediol (see Example I) and replaced in the CLEAN-TRACE devices. The remaining one-third of the swabs were dipped in Solution II containing 5% PG (see Example 1) and replaced in the CLEAN-TRACE devices. Ten separate people were given three replicates of each type of device and were directed to use the test procedure below to evaluate the detectable residue left by the premoistening solution.

Trial Procedure

The premoistened devices prepared as described above were used to swab a 10 cm×10 cm square stainless steel coupon. Three performance traits were measured. First, the ease with which the swab wiped the surface of the coupon was noted. The procedure was repeated for swabs treated with each solution. Second, the steel coupons were dried under ambient conditions for 5 minutes and the appearance of any visible moisture residue was measured. Third, the surface of the coupon was rubbed with a fingertip to assess whether the swabbed surface felt sticky or oily. The criteria used to rate each performance trait is shown in Table 6. Eight different people were given three of each of the different devices (0% PG, 2% PG, and 5% PG) and were instructed to follow the test protocol and rate the performance of each type. The results are presented in Table 7.

TABLE 6

Criteria for evaluating the performance of premoistened sample-collecting devices. In this experiment, the control was a clean dry stainless steel coupon.

| Rating | Swab Effectiveness | Visible Residue | Tactile residue |
|---|---|---|---|
| 1 | Slides over coupon very easily | No visible residue | Feels no different than control |
| 2 | Smooth swabbing action | Slight residue/watermark | Can feel some slight residue |
| 3 | Some drag on swab | Some noticeable residue | Feels soiled |
| 4 | Difficult to swab | Obvious residue | Feels noticeably soiled |
| 5 | Extremely difficult to swab. | Clearly very soiled | Feels heavily soiled. |

TABLE 7

Performance testing results. The results represent average ratings (according to the criteriain Table 6) from eight people who tested three of each swab type.

| Swab Type | Swab Effectiveness | Visible Residue | Tactile residue |
|---|---|---|---|
| 5% PG | 2.5 | 2.9 | 1.5 |
| 2% PG | 2.8 | 3.8 | 1.5 |
| Control | 2.4 | 4.1 | 1.5 |

Example 5

Performance Evaluation of Various Materials

Swabs were prepared as described in Example 1. Aliquots of Solution II were prepared with each of the materials listed in Table 8 and at the concentrations listed in Table 8. The swabs were tested for moisture retention as described in Example 1, for compatibility with luciferase enzyme as described in Example 3, and for perdurable detectable residue as described in Example 4. In these experiments, the swab effectiveness parameter was not recorded. The results are shown in Table 8. All concentrations are listed as percent weight/volume. Solution I-moistened swabs were used as controls for all comparisons. Inhibition of luciferase activity was scored as significant when the measurement from the test swab was <90% of the activity observed with the control swabs. The inhibition was scored as very significant when the measurement from the test swab was <50% of the activity observed with the control swabs.

TABLE 8

Performance evaluation of various materials used in a premoistened solution for a swabbing device.

| Humectant | Concentrations tested | Moisture retention | *Compatibility with luciferase enzyme | Residue (Visual and Tactile Results) |
|---|---|---|---|---|
| Sorbitol | 1 | No significant improvement with 1%. | No inhibition | Sticky |
|  | 5 | Slight improvement with 5%. | No inhibition | Very sticky |
|  | 10, 20, 30, 40, 50, 100% | Significant improvement with ≥10% | No inhibition up to 50%; 100% not tested | Very sticky |
| Glycerol | 1, 5 | Comparable to sorbitol and propylene glycol (PG) | No inhibition up to 5% | Greasy residue at 5%. Drying time was longer than PG |
|  | 10, 20, 50% | Comparable to sorbitol and propylene glycol (PG) | 10-50% not tested | Greasy residue at 10%. Drying time was longer than PG. |
| Propylene glycol (1,2-propanediol) | 1, 2, 3, 4 | No significant improvement with 1%; some improvement with 2% | No inhibition | Very little residue at 2%; not tested at 1, 3, or 4% |
|  | 5, 6, 8% | Significant improvement ≥5% | No inhibition | Very little residue at 5% and 6% |
|  | 10, 20, 25, 50% | Significant improvement ≥5% | Not tested | Very Greasy/oily with ≥10%. |
| Sodium lactate | 5, 10% | No significant improvement with 5 or 10% soln. | Significant inhibition at 5% | Very little residue at 5%. 10% not tested. |
| Incromectant (N-Acetylethanolamine) | 2, 5, 10% | 5% solution was comparable to PG | Some inhibition at 5% 2% and 10% not tested | Greasy at 2% and 5% |
| Polyethylene glycol 200 MW | 10% | Not tested | Significant inhibition | Greasy droplets, felt greasy |
| Polyethylene glycol 380-420 MW | 10% | Not tested | Significant inhibition | Very greasy residue; surface felt greasy |
| Polypropylene glycol 425 MW** | 10% | Not tested | Significant inhibition | Visible oil slick; felt greasy |

**The swabbing solution with 10% 425-MW-polypropylene glycol was observed to be and remain cloudy. Also polypropylene glycol having a molecular weight of 2700 (PPG2700) was examined. However it was observed that such PPG2700 is immiscible in the swabbing solution, and thus no further testing was conducted.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:

1. A method of detecting an analyte in a sample, the method comprising:
   providing a sample-collecting device comprising a shaft and a porous medium coupled to the shaft, the porous medium comprising an aqueous solution including 1,2-propanediol as a humectant and a cell lysis reagent;
   wherein the porous medium is adapted to collect a sample from a surface;
   wherein the concentration of 1,2-propanediol in the aqueous solution is about 2 weight percent to 8 weight percent;
   contacting the sample-collecting device with a surface to obtain a sample from the surface; and
   detecting the analyte;
   wherein the analyte is a Gram positive bacteria or a Gram negative bacteria.

2. A method according to claim 1, comprising detecting the analyte by a culture method, a genetic assay, a cell detection assay, or an immunoassay.

3. A method according to claim 1, wherein detecting the analyte comprises detecting cells, proteins, or enzyme activity of the Gram positive bacteria or Gram negative bacteria.

4. A method according to claim 3, wherein said enzyme activity comprises at least one of luciferase enzyme activity, phosphatase enzyme activity, and adenylate kinase enzyme activity.

5. A method according to claim 1, wherein the cell lysis reagent comprises a detergent.

6. A method according to claim 1, wherein the cell lysis reagent comprises a chlorhexidine gluconate.

7. A method according to claim 4, wherein said enzyme activity is detected by at least one of colorimetry, fluorimetry, and luminometry.

* * * * *